United States Patent [19]

Tsuji et al.

[11] Patent Number: 5,157,135
[45] Date of Patent: * Oct. 20, 1992

[54] 1α,25-DIHYDROXYVITAMIN D4 COMPOUNDS, ERGOSTA-5,7-DIENE COMPOUNDS AND PROCESSES FOR THE PREPARATION THEREOF

[75] Inventors: Masahiro Tsuji; Yoji Tachibana, both of Kawagoe; Shinji Yokoyama, Ohi; Nobuo Ikekawa, Musashino, all of Japan

[73] Assignee: Nisshin Flour Milling Co., Ltd., Tokyo, Japan

[*] Notice: The portion of the term of this patent subsequent to Feb. 11, 2009 has been disclaimed.

[21] Appl. No.: 496,862

[22] Filed: Mar. 21, 1990

[30] Foreign Application Priority Data

Mar. 31, 1989 [JP] Japan .................. 1-78110

[51] Int. Cl.$^5$ .................. C07C 172/00; C07J 9/00
[52] U.S. Cl. .................................................. 552/653
[58] Field of Search ........................... 552/541, 653

[56] References Cited

U.S. PATENT DOCUMENTS

| | | | |
|---|---|---|---|
| 4,202,829 | 5/1980 | DeLuca et al. | 552/653 |
| 4,717,721 | 1/1988 | DeLuca et al. | 552/541 |
| 4,719,204 | 1/1988 | DeLuca et al. | 552/653 |
| 4,719,205 | 1/1988 | DeLuca et al. | 552/653 |

FOREIGN PATENT DOCUMENTS

| | | | |
|---|---|---|---|
| 0122490 | 10/1984 | European Pat. Off. | 552/653 |
| 0337305 | 10/1989 | European Pat. Off. | 552/653 |
| 63-126862 | 5/1988 | Japan . | |
| 8203864 | 10/1982 | PCT Int'l Appl. | 552/653 |
| 8502189 | 5/1985 | PCT Int'l Appl. | 552/653 |
| 7900513 | 5/1986 | PCT Int'l Appl. | 552/653 |
| 8404527 | 4/1987 | PCT Int'l Appl. | 552/653 |

OTHER PUBLICATIONS

H. F. DeLuca et al., "Tetrahedron Letters", 4147 (1972).
H. F. DeLuca et al., "J. C. S. Perkin I", 165 (1979).
Lam et al., "Steroid", 30, 671 (1977).
Baggiolini, et al. J. Org. Chem 1986 51 3098–3108.
Ochi, et al. J. Chem. Soc. Perkins trans. 1, 1979 (1) 165-9 Chemical Abstracts vol. 91, 1979 Abstract 123925s.
Ogata, et al. Chem. Parm. Bull, 1978 26(10) 2933–40 Chemical Abstracts vol. 90, 1979 Abstract 138096.

*Primary Examiner*—Robert T. Bond
*Assistant Examiner*—E. C. Ward
*Attorney, Agent, or Firm*—Abelman, Frayne & Schwab

[57] ABSTRACT (24S)- and (24R)-1α,25-Dihydroxyvitamin D4 compounds and processes for preparing same. Ergosta-5,7-diene compounds which are useful intermediates in the synthesis of the 1α,25-dihydroxyvitamin D4 compounds. The D4 compounds are expected to possess an interesting pharmacological activity in association with the active-type vitamins D3 and D2.

1 Claim, No Drawings

1α,25-DIHYDROXYVITAMIN D4 COMPOUNDS, ERGOSTA-5,7-DIENE COMPOUNDS AND PROCESSES FOR THE PREPARATION THEREOF

FIELD OF THE INVENTION

This invention relates to new 1α,25-dihydroxyvitamin D4 compounds, new ergosta-5,7-diene compounds which are useful intermediates in the synthesis of those D4 compounds and processes for the preparation of said D4 and diene compounds.

BACKGROUND OF THE INVENTION

The metabolism of vitamin D has been studied and a variety of metabolites have been found. Prior to occurrence of their physiological activity, vitamins D are initially hydroxylated at the 25-carbon thereof in liver to give 25-hydroxyvitamins D, which is then hydroxylated at the 1α-, 24R- or 26-carbons thereof in kidney, thus transforming by metabolism into 1,25-dihydroxyvitamins D, 24,25-dihydroxyvitamins D or 25,26-dihydroxyvitamins D, respectively. Of these metabolites, the 1α,25-dihydroxy derivatives of vitamin $D_2$ or $D_3$ possess highest physiological activity and are considered as a final active product. Further, those active-type vitamins D are used as a remedy for the treatment of bone diseases, renal diseases, parathyroid disorder and the like. In recent years, there is a growing interest due to the discovery of new activities such as differentiation inductive or cell growth inhibitory action.

The active-type vitamin $D_4$ to be sought by the present invention, i.e., (24S)-1α,25-dihydroxyvitamin $D_4$ and the 24-epimer thereof, (24R)-1α,25-dihydroxyvitamin $D_4$ are expected to possess an interesting pharmacological activity in association with the active-type vitamins $D_3$ and $D_2$. However, the above two compounds have not been synthesized for more difficulty in synthesis than the active-type vitamins $D_3$ and $D_2$.

Now, we have investigated the prior art process for the preparation of 1α,25-dihydroxycholecalciferol (1α,25-dihydroxyvitamin $D_3$) by irradiation of 5,7-cholestadiene-1α,3β,25-triol(1α,25-dihydroxy-7-dehydrocholesterol) followed by isomerization (H. F. DeLuca et al, "Tetrahedron Letters", 4147 (1972) and H. F. DeLuca et al, "J. C. S. Perkin I", 165 (1979)), and have found that new (24S)-1α,25-dihydroxyvitamin $D_4$ and the (24R)-epimer thereof are produced from new intermediates, 5,7-ergostadiene-1α,3β,25-triol and the (24R)-epimer thereof.

DETAILED DESCRIPTION OF THE INVENTION

The present invention provides a new 1α,25-dihydroxyvitamin $D_4$ compound of formula (I)

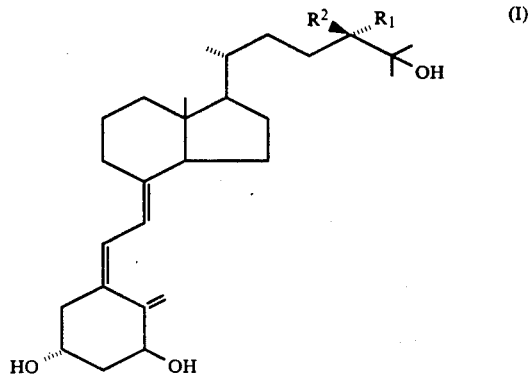

wherein $R_2$ is H when $R_1$ is $CH_3$ (24S form) or $R_2$ is $CH_3$ when $R_1$ is H (24R form). The invention also provides a new intermediate, ergosta-5,7-diene compound of formula (II)

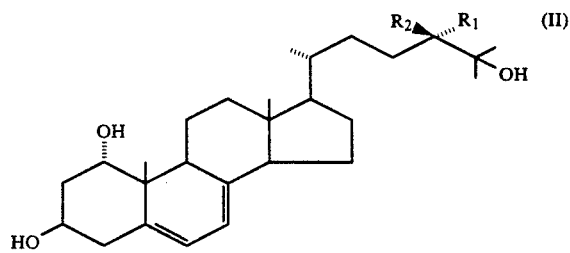

wherein $R_2$ is H when $R_1$ is $CH_3$ or $R_2$ is $CH_3$ when $R_1$ is H.

The compounds of formula (I) can be prepared by the processes illustrated for example by the following reaction scheme I which includes the synthetic route starting from the compound (III) via a new intermediate, the compound (II).

SCHEME I

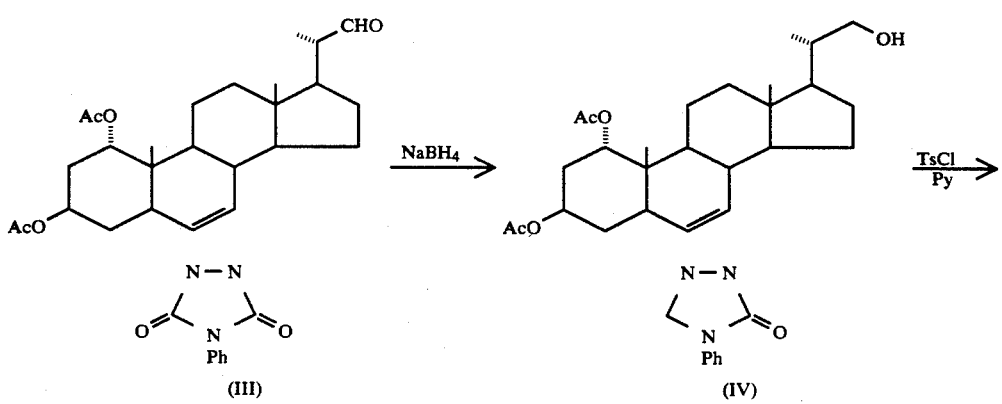

SCHEME I
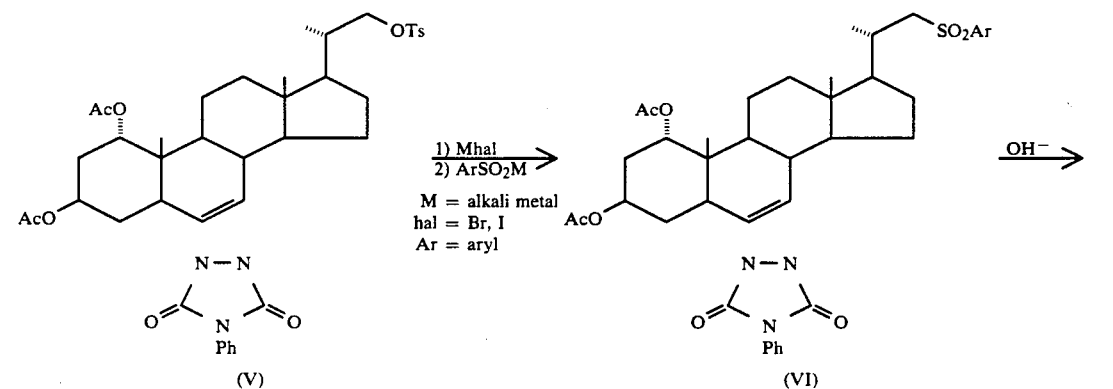
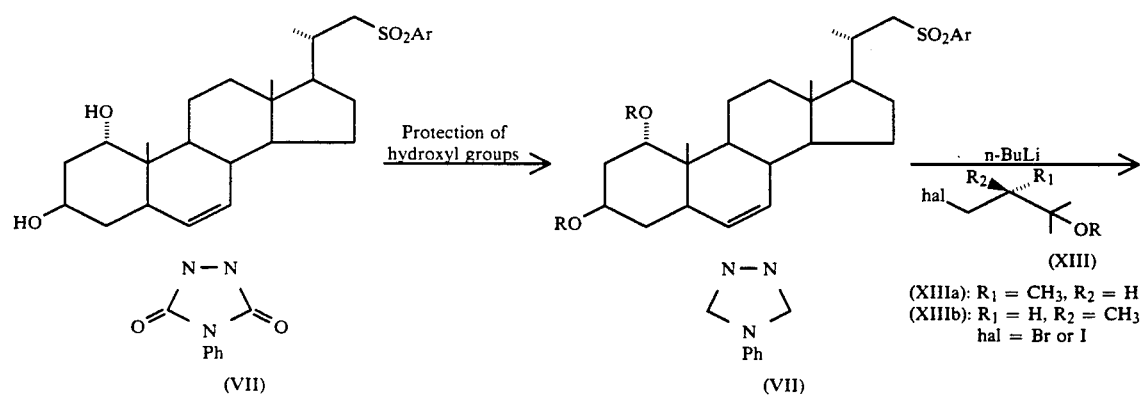
R = protecting group for hydroxyl
(XIIIa): R₁ = CH₃, R₂ = H
(XIIIb): R₁ = H, R₂ = CH₃
hal = Br or I
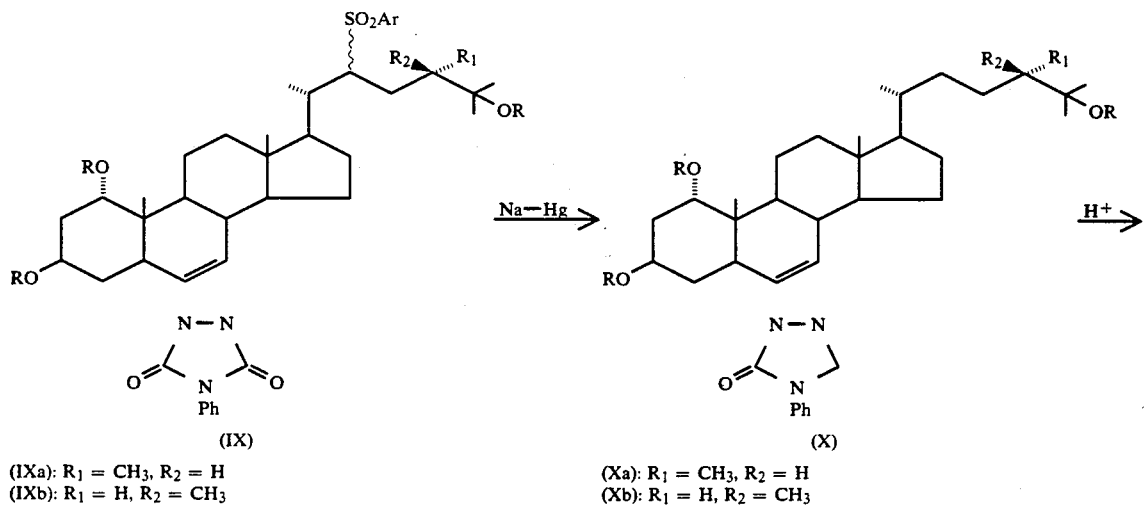
(IXa): R₁ = CH₃, R₂ = H
(IXb): R₁ = H, R₂ = CH₃
(Xa): R₁ = CH₃, R₂ = H
(Xb): R₁ = H, R₂ = CH₃

-continued
SCHEME I

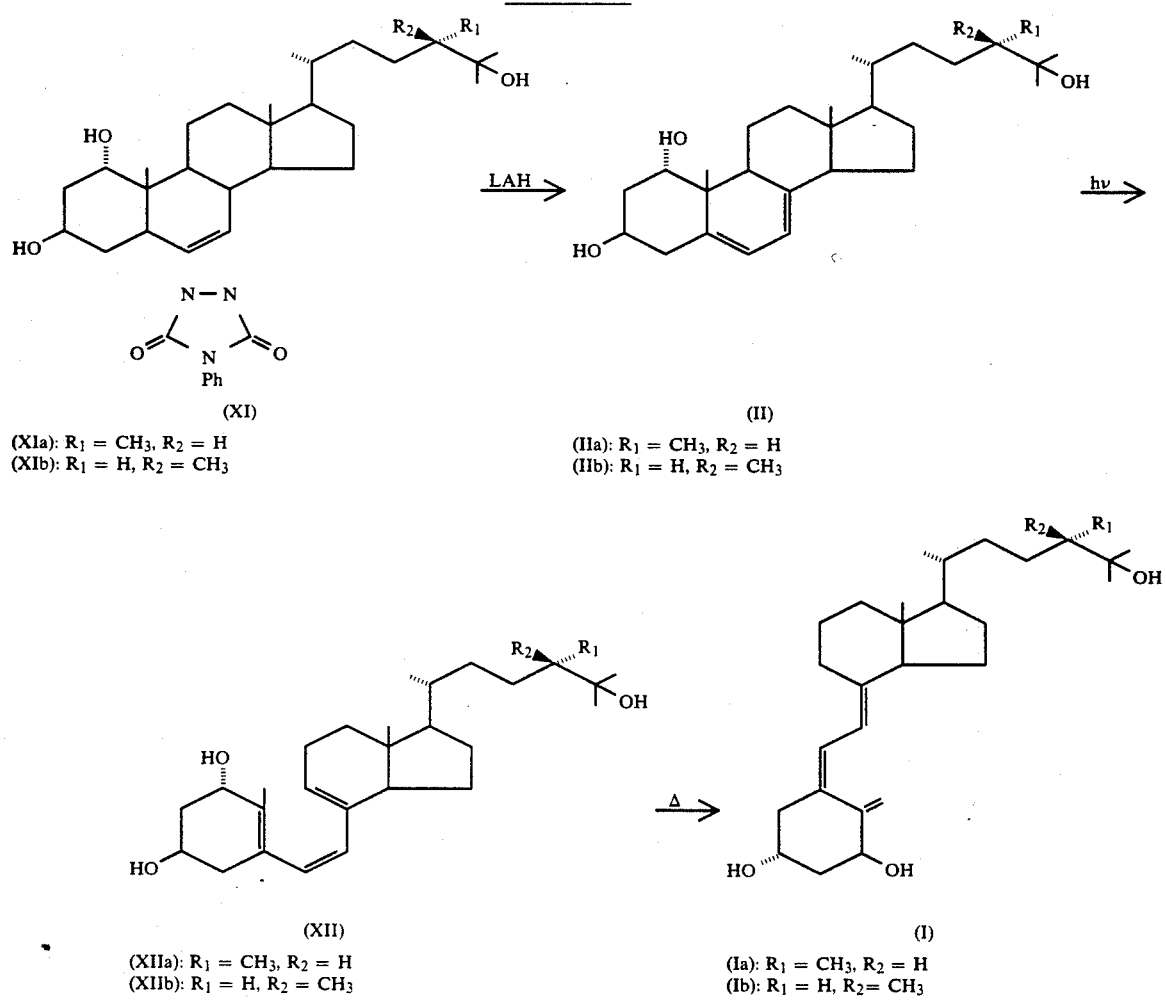

(XIa): R₁ = CH₃, R₂ = H
(XIb): R₁ = H, R₂ = CH₃

(IIa): R₁ = CH₃, R₂ = H
(IIb): R₁ = H, R₂ = CH₃

(XIIa): R₁ = CH₃, R₂ = H
(XIIb): R₁ = H, R₂ = CH₃

(Ia): R₁ = CH₃, R₂ = H
(Ib): R₁ = H, R₂ = CH₃

In the above scheme, an aldehyde compound of formula (III) used as a starting material can be prepared by protecting with 4-phenyl-1,2,4-triazoline-3,5-dione the 5,7-diene of (22E)-5,7,22-ergostatriene-1α,3β-diol diacetate of formula (XIV) prepared in accordance with known method (Japanese Patent Kokai 63-126862, or "Steroid", 30, 671 (1977)), followed by oxidation of the protected compound at the 22-olefin with ozone. The synthesis route is shown by the following scheme II.

SCHEME II

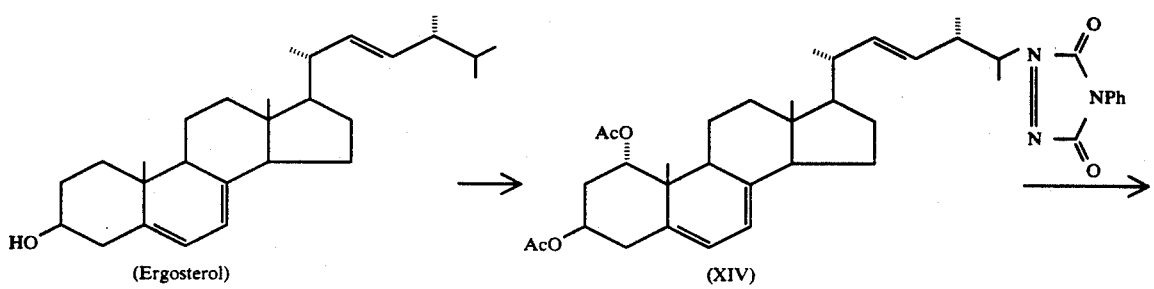

(Ergosterol)

(XIV)

-continued
SCHEME II

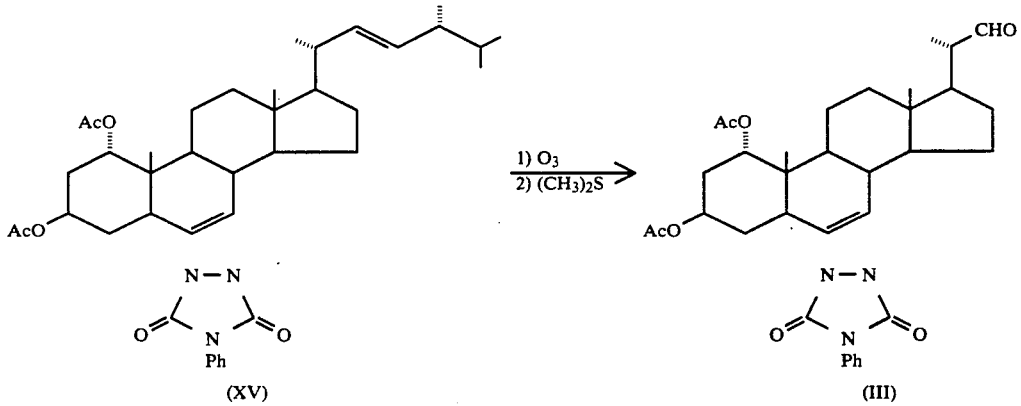

(XV) → (III)

As illustrated in scheme I, the compound of formula (III) is reduced with sodium borohydride (NaBH$_4$) to afford an alcohol of formula (IV).

This reaction is carried out in an organic solvent, e.g. alcohol solvents such as methanol or ethanol or mixed solvents thereof with halogen solvents such as chloroform or methylene chloride.

The alcohol (IV) is converted into a tosylate (V) in a conventional manner, i.e. using p-toluenesulfonyl chloride in pyridine. Then, the tosylate (V) is treated with an alkali metal halide, e.g., sodium iodide in N,N-dimethyl formamide to give a halide, e.g. iodide, which without isolation is reacted with an alkali metal salt of an aryl sulfinic acid, e.g., sodium benzenesulfinate, sodium toluenesulfinate to afford a sulfone of formula (VI).

The sulfone (VI) is subjected to saponification reaction with an alkali to give a diol (VII). The hydroxyl groups present in the diol (VII) are protected by suitable protecting group conventionally employed for the protection of hydroxyl, preferably one stable under basic conditions but removable under acidic conditions, in a conventional manner to give a protected sulfone of formula (VIII). The protecting groups include, e.g., tetrahydropyranyl, tetrahydrofuranyl, methoxymethyl, 1-ethoxyethyl, trimethylsilyl, tert.-butyldimethylsilyl or the like.

The sulfone (VIII) is reacted with a halide (XIII) to give an alkylated sulfone compound (IX).

This reaction is carried out by forming an anion of the sulfone (VIII) with a strong organic base such as n-butyllithium or lithium diisopropylamide (LDA) in tetrahydrofuran at a temperature between −78° C. and −60° C., if desired, in the presence of hexamethylphosphoric triamide (HMPA), followed by addition of the halide (XIII) at a temperature between −30° C. and −20° C. The amount of the organic base used is in a range of 1.0 to 3.0 moles, preferably 1.0 to 1.3 moles per mole of the sulfone (VIII). The amount of the halide (XIII) used is in a range of 1 to 10 moles, preferably 1.5 to 5 moles per mole of the sulfone (VIII).

further, an optically active halide of formula (XIII) can be prepared from a commercially available optically active methyl (S)-(+)-3-hydroxy-2-methylpropionate (R$_1$=CH$_3$, R$_2$=H) and methyl (R)-(−)-3-hydroxy-2-methylpropionate (R$_1$=H, R$_2$=CH$_3$) as shown in the following scheme III.

SCHEME III

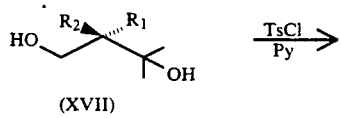

(XVI)

(XVIa): R$_1$ = CH$_3$, R$_2$ = H
(XVIb): R$_1$ = H, R$_2$ = CH$_3$

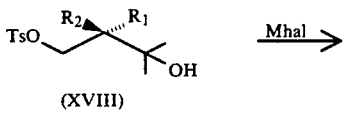

(XVII)

(XVIIa): R$_1$ = CH$_3$, R$_2$ = H
(XVIIb): R$_1$ = H, R$_2$ = CH$_3$

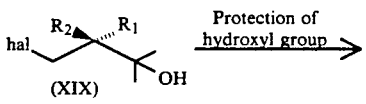

(XVIII)

(XVIIIa): R$_1$ = CH$_3$, R$_2$ = H
(XVIIIb): R$_1$ = H, R$_2$ = CH$_3$

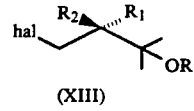

(XIX)

(XIXa): R$_1$ = CH$_3$, R$_2$ = H
(XIXb): R$_1$ = H, R$_2$ = CH$_3$

M = Li, Na or K
hal = Br or I

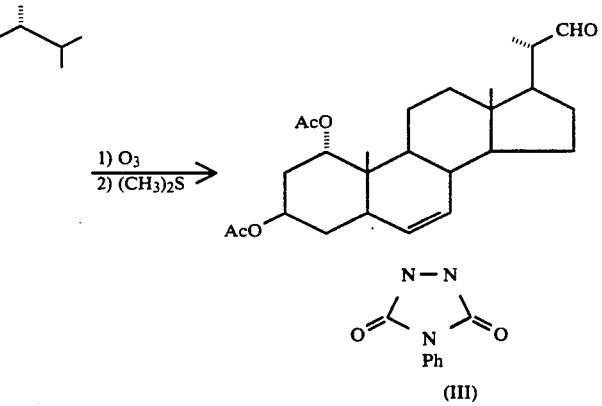

(XIII)

(XIIIa): R$_1$ = CH$_3$, R$_2$= H
(XIIIb): R$_1$ = H, R$_2$ = CH$_3$

R = protecting group for hydroxyl

The sulfone compound of formula (IX) is treated with an excess amount of sodium amalgam in a mixed solvent of ethyl acetate and methanol or in methanol saturated with disodium hydrogenphosphate (Na$_2$HPO$_4$) to eliminate the sulfone, thus affording a compound of formula (X). The reaction is conducted at a temperature between −40° C. and room temperature.

Alternatively, the compound (X) can be prepared from compound (V) by the method as shown in the following scheme IV.

ature between −78° C. and −60° C., if desired in the presence of hexamethylphosphoric triamide (HMPA), followed by addition of the halide (XXII) at a tempera-

SCHEME IV

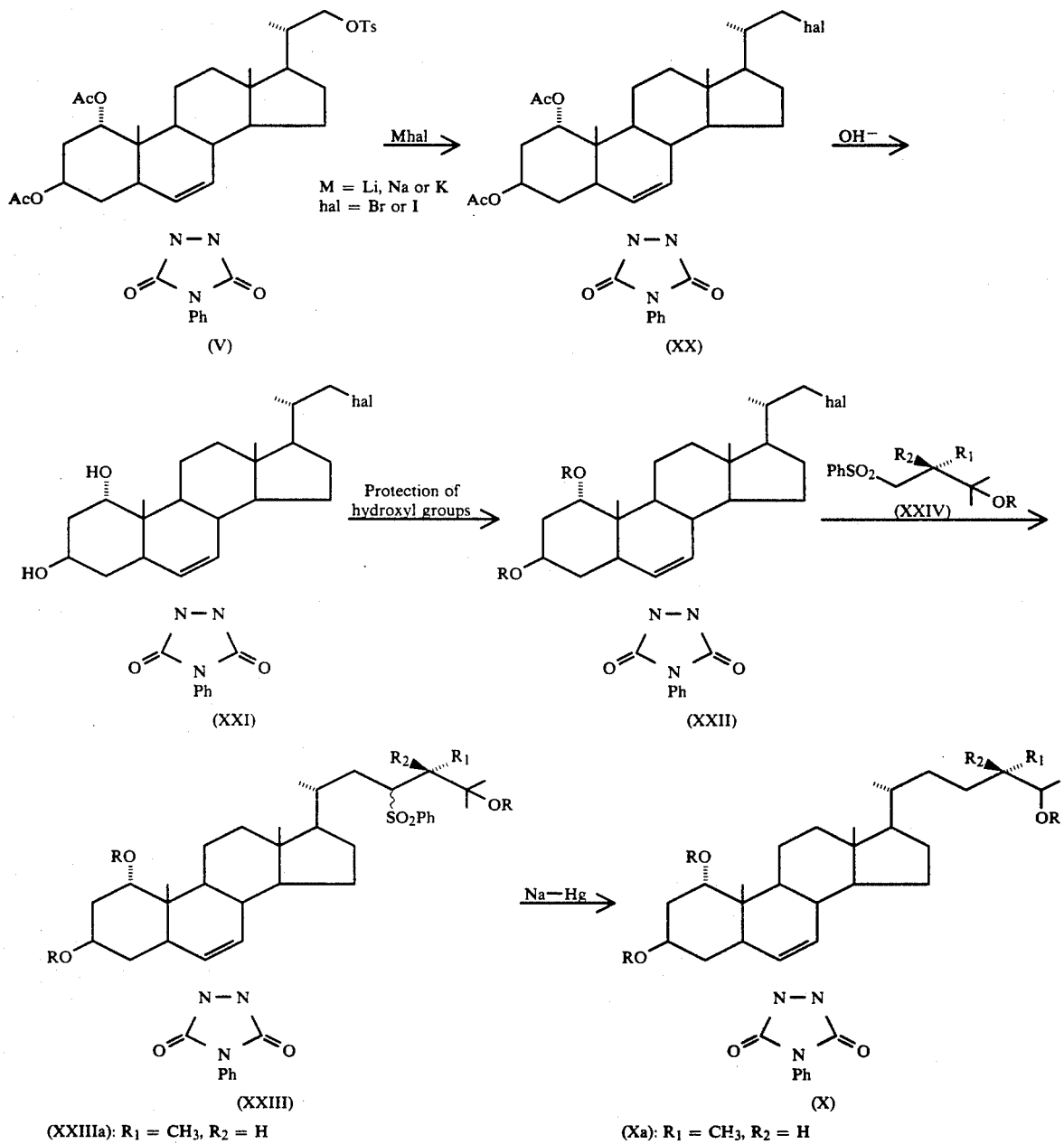

(XXIIIa): $R_1 = CH_3$, $R_2 = H$
(XXIIIb): $R_1 = H$, $R_2 = CH_3$ (Xa): $R_1 = CH_3$, $R_2 = H$
(Xb): $R_1 = H$, $R_2 = CH_3$

The tosylate (V) is treated with an alkaline metal halide in a solvent such as N,N-dimethylformamide, acetone or methyl ethyl ketone to give a halide (XX). Subsequently, the halide (XX) is subjected to saponification reaction with an alkali to give a diol (XXI). The hydroxyl groups present in the diol (XXI) are protected in a similar way as described for the diol to give a halide of formula (XXII).

The halide (XXII) is reacted with a sulfone (XXIV) to afford an alkylated sulfone compound (XXIII). This reaction is carried out by forming an anion of the sulfone (XXIV) with a strong organic base such as n-butyllithium or lithium diisopropylamide (LDA) at a temperture between −30° C. and −20° C. The amount of the sulfone (XXIV) used is in a range of 1 to 10 moles, preferably 1.5 to 5 moles per mole of the halide (XXII). The amount of the organic base used is in a range of 1.0 to 3.0 moles, preferably 1.0 to 1.3 moles per mole of the sulfone (XXIV).

Further, an optically active sulfone compound of formula (XXIV) can be prepared from the compound of formula (XVIII) as shown in the following scheme V.

SCHEME V

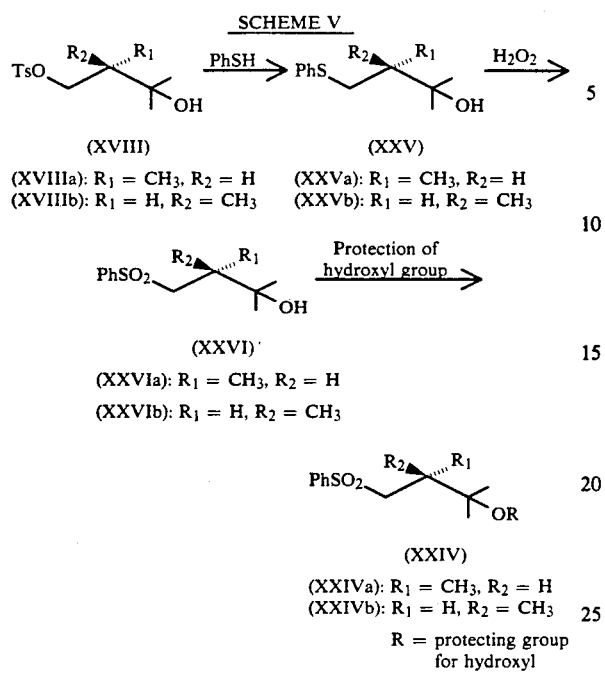

(XVIII)
(XVIIIa): $R_1 = CH_3$, $R_2 = H$
(XVIIIb): $R_1 = H$, $R_2 = CH_3$ (XXV)
(XXVa): $R_1 = CH_3$, $R_2 = H$
(XXVb): $R_1 = H$, $R_2 = CH_3$ (XXVI)
(XXVIa): $R_1 = CH_3$, $R_2 = H$
(XXVIb): $R_1 = H$, $R_2 = CH_3$ (XXIV)
(XXIVa): $R_1 = CH_3$, $R_2 = H$
(XXIVb): $R_1 = H$, $R_2 = CH_3$

R = protecting group for hydroxyl

The sulfone compound of formula (XXIII) is treated in a similar manner for the sulfone compound of formula (IX) to form a compound of formula (X).

Removal of the protecting groups for the 1α,3β,25-hydroxyl groups from the compound of formula (X) affords a triol of formula (XI) wherein the 5,7-diene is protected. This removal of the protecting group is carried out in a conventional manner under acidic conditions. For example, the reaction is carried out under acidic conditions such as acetic acid/water or acetic acid/water/tetrahydrofuran or by treatment with p-toluenesulfonic acid, pyridinium p-toluenesulfonate, Amberlist ® 15 and the like, in methanol or ethanol. Preferably, this reaction is carried out in ethanol at a temperature between 50° C. and 80° C. using p-toluene sulfonic acid in an amount of 0.1 to 0.3 moles per mole of the compound (X).

Removal of the protecting group at the 5,7-diene from the compound of formula (XI) affords a 5,7-diene compound of formula (II). This reaction is performed by a conventional way, for example using an excess amount of lithium aluminum hydride (LiAlH₄) for the compound of formula (XI) in tetrahydrofuran at a temperature at which tetrahydrofuran boils.

The 5,7-diene compound of formula (II) can be converted into a vitamin D derivative of formula (I) by a general procedure for the synthesis of vitamins D from the 5,7-diene compounds. For instance, the 5,7-diene compound of formula (II) is subjected to irradiation in ether or ether/tetrahydrofuran to afford a previtamin D of formula (XII). The previtamin D (XII), after purification by chromatography or without purification, is isomerized by heating in a suitable solvent, e.g. ethanol. Purification of the resulting products by chromatography and recrystallization affords a vitamin D derivative of formula (I).

The invention is further illustrated by the following non-limitative examples.

EXAMPLE 1

5α,8α-(4-Phenyl-1,2-urazolo)-23,24-dinor-6-cholene-1α,3β,22-triol 1α,3β-diacetate (IV)

To a solution of 22-oxo-5α,8α-(4-phenyl-1,2-urazolo)-23,24-dinor-6-cholene-1α,3β-diol diacetate (III) (9.50 g, 15.8 mmol) in methanol (100 ml) was added sodium borohydride (0.30 g, 7.9 mmol) in several portions with stirring at room temperature. After stirring for 10 minutes, acetic acid (0.3 ml) was added with additional stirring for 10 minutes. The reaction solution was distilled under reduced pressure to remove methanol. The residue with the addition of water was extracted with chloroform. The chloroform layer was washed with water and then a saturated sodium chloride solution and dried over anhydrous magnesium sulfate and concentrated to give 9.50 g of the crude title compound (IV) as the residue. The product was used for the next step without further purification. A sample for analysis was prepared by recrystallization from hexane-ethyl acetate.

m.p. 203°-205° C.

$[\alpha]_D^{25} -117°$ C. (c = 1.07, CHCl₃)

IR (KBr) 3440, 1740, 1695, 1680, 1605, 1510, 1410, 1370, 1250, 1235, 1100, 1035 cm⁻¹

NMR (CDCl₃)δ 0.85(3H, s, 18-H₃) 1.05(3H, d, J=6.3 Hz, 21-H₃) 1.06(3H, s, 19-H₃)

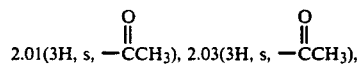

2.01(3H, s, —CCH₃), 2.03(3H, s, —CCH₃), 3.27 (1H, dd, J₁=4.9 Hz, J₂=13 Hz, 9-H) 3.32 (1H, dd, J₁=6.9 Hz, J₂=10.6 Hz, 22-H) 3.64(1H, dd, J₁=3.7 Hz, J₂=10.6 Hz, 22-H) 5.11(1H, m, 1-H) 5.88(1H, m, 3-H) 6.33 & 6.45(2H, AB_q, J=8.3 Hz, 6-H & 7-H) 7.28-7.52(5H, m, —Ar—H)

mass spectrum: m/e 430(M+- triazoline, 0.5), 370(7), 310(100), 251(8), 197(73)

EXAMPLE 2

5α,8α-(4-Phenyl-1,2-urazolo)-23,24-dinor-6-cholene-1α,3β,22-triol 1α,3β-diacetate 22-p-toluene sulfonate (V)

The crude 5α,8α-(4-phenyl-1,2-urazolo)-23,24-dinor-6-cholene-1α,3β,22-triol 1α,3β-diacetate (IV) (9.50 g) prepared in Example 1 was dissolved in dry pyridine (45 ml) and p-toluenesulfonyl chloride (4.50 g, 23.6 mmol) was added with stirring under ice-cooling. The reaction mixture was stirred at the same temperature for 24 hrs. Water was added to the reaction solution, the solution was stirred for one hour and then poured into an ice water and extracted with chloroform. The chloroform layer was washed successively with water, 5% hydrochloric acid, a saturated sodium hydrogencarbonate solution and a saturated sodium chloride solution, dried over anhydrous magnesium sulfate and concentrated. The residue was purified by silica gel chromatography (eluted with 1/1 and then 1/2 hexane/ethyl acetate) to give 9.33 g of the title compound (V).

IR (KBr) 1750, 1700, 1600, 1505, 1400, 1245, 1180, 1030 cm⁻¹

NMR (CDCl₃) δ 0.80(3H, s, 18-H₃) 1.01(3H, d, J=6.6 Hz, 21-H₃) 1.05(3H, s, 19-H₃)

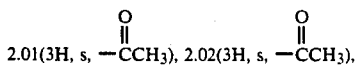

2.44 (3H, s, —Ar—p—CH₃) 3.25(1H, dd, J₁=5.6 Hz, J₂=13.4 Hz, 9-H) 3.73(1H, dd, J₁=6.6 Hz, J₂8.8 Hz, 22-H) 4.01(1H, dd, J₁=2.4 Hz, J₂=8.8 Hz, 22-H) 5.09(1H, m, 1-H) 5.87(1H, m, 3-H) 6.33 & 6.41(2H, AB$_q$, J=8.3 Hz, 6-H & 7-H) 7.32-7.50(7H, m, —Ar—H) 7.77 (2H, d, J=8.1 Hz,

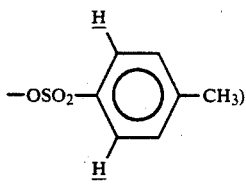

mass spectrum: m/e 524(M+- triazoline-acetic acid, 3), 464(58), 292(43), 277(16), 177(62), 155(100), 119(78)

EXAMPLE 3

22-Phenylsulfonyl-5α,8α-(4-phenyl-1,2-urazolo)-23,24-dinor-6-cholene-1α,3β-diol diacetate (VI)

A solution of 5α,8α-(4-phenyl-1,2-urazolo)-23,24-dinor-6-cholene-1α,3β,22-triol 1α,3β-diacetate 22-p-toluenesulfonate (V) (9.30 g, 12.3 mmol) prepared in Example 2 and sodium iodide (9.19 g, 61.3 mmol) in dry N,N-dimethylformamide (80 ml) was stirred at 80° C. for 30 minutes. Sodium benzenesulfinate (4.02 g, 24.5 mmol) was added and the solution was stirred at 80° C. for 30 minutes. The reaction solution was poured into an ice water and extracted with chloroform. The chloroform layer was washed with water, 5% sodium thiosulfate solution and a saturated sodium chloride solution, dried over anhydrous magnesium sulfate and concentrated. The residue was purified by silica gel chromatography (eluted with 1/1 and then 1/2 hexane/ethyl acetate) to give 7.31 g of the title compound (VI). The product was used for the next step without further purification. A sample for analysis was prepared by recrystallization from hexane-ethyl acetate.

m.p. 176°-178° C.
[α]$_D^{23}$ −99.3° (c=1.20, CHCl₃)
IR (KBr) 1750, 1695, 1600, 1505, 1400, 1305, 1250, 1235, 1145 cm⁻¹
NMR (CDCl₃) δ 0.83(3H, s, 18-H₃) 1.05(3H, s, 19-H₃) 1.21(3H, d, J=6.4 Hz, 21-H₃)

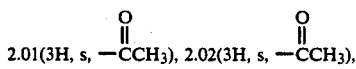

2.84 (1H, dd, J₁=9.4 Hz, J₂=13.8 Hz, 22-H) 3.13 (1H, d, J=13.8 Hz, 22-H) 3.25(1H, dd, J₁=5.6 Hz, J₂=13.9 Hz, 9-H) 5.09(1H, m, 1-H) 5.89(1H, m, 3-H) 6.33 & 6.41(2H, AB$_q$, J=8.3 Hz, 6-H & 7-H) 7.30-7.70(8H, m, —Ar—H) 7.89(2H, m, —Ar—H)

mass spectrum: m/e 494(M+- triazoline-acetic acid, 10), 435(100), 251(18), 177(48), 141(82)

EXAMPLE 4

22-Phenylsulfonyl-5α,8α-(4-phenyl-1,2-urazolo)-23,24-dinor-6-cholene-1α,3β-diol (VII)

A solution of potassium hydroxide (1.12 g, 20.0 mmol) in methanol (100 ml) was added to 22-phenylsulfonyl-5α,8α-(4-phenyl-1,2-urazolo)-23,24-dinor-6-cholene-1α,3β-diol diacetate (VI) (7.31 g, 10.0 mmol) obtained in Example 3 and the mixed solution was stirred under reflux for 30 minutes. After cooling, the crystals precipitated were filtered, washed with methanol and dried to give 5.12 g of the title compound (VII).

m.p. 240°-242° C.
[α]$_D^{25}$ −87.3° (c=0.49, CHCl₃)
IR (KBr) 3540, 3470, 1740, 1675, 1505, 1410, 1310, 1155, 1090, 1040 cm⁻¹
NMR (CDCl₃) δ 0.82(3H, s, 18-H₃) 0.90(3H, s, 19-H₃) 1.23(3H, d, J=6.4 Hz, 21-H₃) 2.82(1H, dd, J₁=8.1 Hz, J₂=13.7 Hz, 22-H) 3.10 (2H, m, 9-H & 22-H) 3.81(1H, m, 1-H) 4.84(1H, m, 3-H) 6.25 & 6.36(2H, AB$_q$, J=8.1 Hz, 6-H & 7-H) 7.30-7.70(8H, m, —Ar—H) 7.91(2H, m, —Ar—H)

mass spectrum: m/e 470(M+- triazoline, 5), 452(2), 434(4), 239(21), 177(53), 119(100)

EXAMPLE 5

22-Phenylsulfonyl-5α,8α-(4-phenyl-1,2-urazolo)-1α,3β-bis(tetrahydropyranyloxy)-23,24-dinor-6-cholene (VIII)

A solution of 22-phenylsulfonyl-5α,8α-(4-phenyl-1,2-urazolo)-23,24-dinor-6-cholene-1α,3β-diol (VII) (5.12 g, 7.9 mmol) obtained in Example 4, dihydropyran (2.67 g, 31.8 mmol) and pyridinium p-toluenesulfonate (0.40 g, 1.6 mmol) in dry methylene chloride (50 ml) was stirred at room temperature for 24 hrs. The reaction solution was washed with a saturated sodium hydrogencarbonate solution and a saturated sodium chloride solution, dried over anhydrous magnesium sulfate and then concentrated. The residue was purified by silica gel chromatography (eluted with 2/1 hexane/ethyl acetate) and then recrystallized from hexane-ethyl acetate to give 5.81 g of the title compound (VIII).

m.p. 181°-186° C.
[α]$_D^{24}$ −84.9° (c=1.03, CHCl₃)
IR (KBr) 1750, 1695, 1605, 1505, 1400, 1305, 1150, 1030 cm⁻¹
NMR (CDCl₃) δ 0.83(3H, s, 18-H₃) 0.95 & 0.98(3H, pair of s, 19-H₃) 1.23(3H, d, J=6.4 Hz, 21-H₃) 2.85(1H, m, 22-H) 3.15(2H, m, 9-H & 22-H)

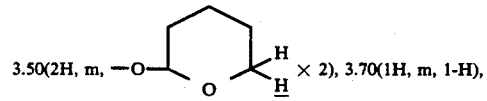

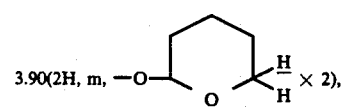

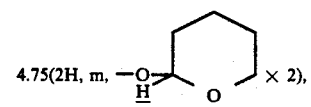

4.85(1H, m, 3-H) 6.32(2H, m, 6-H & 7-H) 7.3-7.7(8H, m, —Ar—H) 7.91(2H, m, —Ar—H)

mass spectrum: m/e 638(M+-triazoline, 0.5), 554(2), 536(2), 239(13), 177(62), 119(100)

EXAMPLE 6

(24S)-22ξ-Phenylsulfonyl-5α,8α-(4-phenyl-1,2-urazolo)-1α,3β,25-tris(tetrahydropyranyloxy)-6-ergostene (IXa)

To a solution of 22-phenylsulfonyl-5α,8α-(4-phenyl-1,2-urazolo)-1α,3β-bis(tetrahydropyranyloxy)-23,24-dinor-6-cholene (VIII) (3.50 g, 4.3 mmol) prepared in Example 5 in dry tetrahydrofuran (35 ml) was added successively n-butyllithium (1.5N hexane solution, 3.4 ml, 5.1 mmol) and dry hexamethylphosphoric triamide (2.26 ml, 12.9 mmol) at −78° C. under argon gas stream and then the solution was stirred at −20° C. for 20 minutes. Subsequently, a solution of (3R)-4-iodo-2,3-dimethyl-2-butanol tetrahydropyranyl ether (XIIIa) (4.03 g, 12.9 mmol) in dry tetrahydrofuran (12 ml) was added at the same temperature and the solution was further stirred for 1.5 hrs. The reaction solution was poured into a saturated ammonium chloride solution and extracted with chloroform. The chloroform layer was washed with a saturated sodium chloride solution, dried over anhydrous magnesium sulfate and then concentrated. The residue was purified by silica gel chromatography (eluted with successively 2/1, 3/2 and 1/1 hexane/ethyl acetate) to give 1.90 g of the title compound (IXa) as a first fraction, recovering 1.34 g of the compound (VIII) as a second fraction.

IR (KBr) 1750, 1695, 1605, 1505, 1400, 1150, 1130, 1075, 1030, 985 cm$^{-1}$

NMR (CDCl$_3$) δ 3.05(1H, m, 22-H) 3.22(1H, m, 9-H)

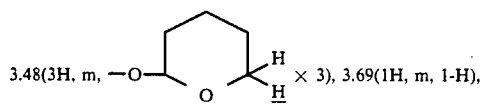

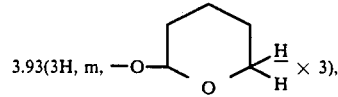

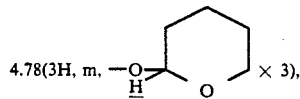

4.93(1H, m, 3-H) 6.33(2H, m, 6-H & 7-H) 7.3–7.9(10H, m, —Ar—H)

EXAMPLE 7

(24R)-22ξ-Phenylsulfonyl-5α,8α-(4-phenyl-1,2-urazolo)-1α,3β,25-tris(tetrahydropyranyloxy)-6-ergostene (IXb)

In a similar manner as in Example 6, from 22-phenylsulfonyl-5α,8α-(4-phenyl-1,2-urazolo)-1α,3β-bis(tetrahydropyranyloxy)-23,24-dinor-6-cholene (VIII) (2.55 g, 3.1 mmol) prepared in Example 5 and (3S)-4-iodo-2,3-dimethyl-2-butanol tetrahydropyranyl ether (XIIIb) (2.93 g, 9.4 mmol), 1.43 g of the title compound (IXb) was obtained and 1.17 g of the compound (VIII) was recovered.

IR (KBr) 1750, 1695, 1605, 1505, 1400, 1150, 1130, 1080, 1030, 985 cm$^{31\ 1}$

NMR (CDCl$_3$) δ 3.18(2H, m, 9-H & 22-H)

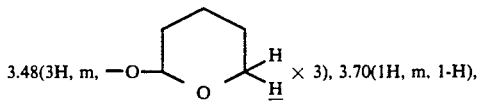

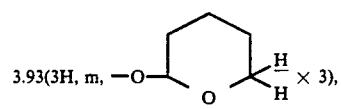

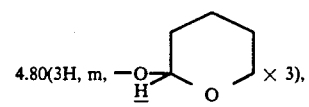

4.92(1H, m, 3-H) 6.32(2H, m, 6-H & 7-H) 7.3–7.9(10H, m, —Ar—H)

EXAMPLE 8

(24S)-5α,8α-(4-Phenyl-1,2-urazolo)-1α,3β,25-tris(tetrahydropyranyloxy)-6-ergostene (Xa)

(24S)-22ξ-Phenylsulfonyl-5α,8α-(4-phenyl-1,2-urazolo)-1α,3β,25-tris(tetrahydropyranyloxy)-6-ergostene (IXa) (1.20 g, 1.20 mmol) prepared in Example 6 was dissolved in methanol (120 ml) saturated with disodium hydrogenphosphate, sodium amalgam (5%, 16.6 g, 36.0 mmol) was added and the mixture was stirred at room temperature for 16 hrs. The supernatant was taken and methanol was distilled off under reduced pressure, to the residue was added water and the mixture was extracted with chloroform. The chloroform layer was washed with water and a saturated sodium chloride solution, dried over anhydrous magnesium sulfate and then concentrated. The residue was purified by silica gel chromatography (eluted with 3/1 and then 2/1 hexane/ethyl acetate) to give 0.51 g of the title compound (Xa).

IR (KBr) 1750, 1700, 1605, 1505, 1400, 1135, 1080, 1030, 985 cm$^{-1}$

NMR (CDCl$_3$) δ 3.22(1H, m, 9-H)

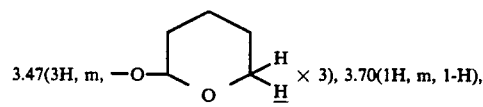

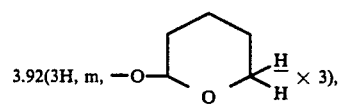

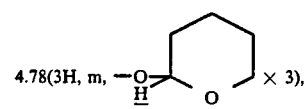

4.93(1H, m, 3-H) 6.37(2H, m, 6-H & 7-H) 7.3–7.5(5H, m, —Ar—H)

mass spectrum: m/e 598(M$^+$- triazoline-dihydropyran, 4), 580(1), 412(80), 239(18), 177(85), 119(100)

EXAMPLE 9

(24R)-5α,8α-(4-Phenyl-1,2-urazolo)-1α,3β,25-tris(tetrahydropyranyloxy)-6-ergostene (Xb)

In a similar manner as in Example 8, 0.78 g of the title compound (Xb) was obtained from (24R)-22ξ-phenylsulfonyl-5α,8α-(4-phenyl-1,2-urazolo)-1α,3β,25-tris(tetrahydropyranyloxy)-6-ergostene (IXb) (1.71 g, 1.7 mmol) prepared in Example 7.

IR (KBr) 1750, 1695, 1600, 1505, 1395, 1130, 1075, 1025, 985 cm$^{-1}$

NMR (CDCl$_3$) δ 3.20 (1H m, 9-H)

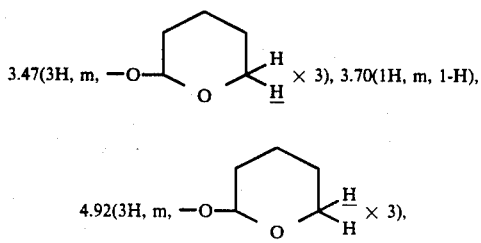

3.47(3H, m, —O—[pyranyl] × 3), 3.70(1H, m, 1-H), 4.92(3H, m, —O—[pyranyl] × 3), 4.93(1H, m, 3-H) 6.37(2H, m, 6-H & 7-H) 7.3–7.5(5H, m, —Ar—H)

EXAMPLE 10

(24S)-5α,8α-(4-Phenyl-1,2-urazolo)-6-ergostene-1α,3β,25-triol (XIa)

A solution of (24S)-5α,8β-(4-phenyl-1,2-urazolo)-1α,3β,25-tris(tetrahydropyranyloxy)-6-ergostene (Xa) (0.51 g, 0.60 mmol) prepared in Example 8 and p-toluenesulfonic acid monohydrate (23 mg, 0.12 mmol) in 95% ethanol (5 ml) was stirred at 80° C. for 4 hrs. From the reaction solution was distilled off ethanol under reduced pressure and the residue to which was added a saturated sodium chloride solution was extracted with chloroform. The chloroform layer was dried over anhydrous magnesium sulfate and then concentrated. The residue was purified by silica gel chromatography (eluted with ¼ chloroform/ethyl acetate and then ethyl acetate) to give 0.31 g of the title compound (Xa). A sample for analysis was prepared by recrystallization from ethyl acetate (the crystals containing ¼ EtOAc).

m.p. 211°–214° C.

$[\alpha]_D^{22}$ −97.7° (c=0.31, CHCl$_3$)

IR (KBr) 3530, 3460, 1745, 1680, 1505, 1410, 1320, 1150, 1035 cm$^{-1}$

NMR (CDCl$_3$) δ 0.81(3H, s, 18-H$_3$) 0.88(3H, d, J=7.1 Hz, 28-H$_3$) 0.92(3H, s, 19-H$_3$) 0.94(3H, d, J=6.4 Hz, 21-H$_3$) 1.14 & 1.15(6H, each s, 26-H$_3$ & 27-H$_3$) 3.12(1H, dd, J$_1$=6.1 Hz, J$_2$=15.6 Hz, 9-H) 3.85(1H, m, 1-H) 4.88(1H, m, 3-H) 6.25 & 6.41(2H, AB$_q$, J=8.5 Hz, 6-H & 7-H) 7.3–7.4(5H, m, —Ar—H)

mass spectrum: m/e 430(m$^+$- triazoline, 13), 412(12), 394(11), 251(17), 199(41), 119(100)

EXAMPLE 11

(24R)-5α,8α-(4-Phenyl-1,2-urazolo)-6-ergostene-1α,3β,25-triol (XIb)

In a similar way as in Example 10, 0.45 g of the title compound (XIb) was obtained from (24R)-5α,8α-(4-phenyl-1,2-urazolo)-1α,3β,25-tris(tetrahydropyranyloxy)-6-ergostene (Xb) (0.77 g, 0.90 mmol) prepared in Example 9.

m.p. 216°–218° C.

$[\alpha]_D^{22}$ −79.0° (c=0.36, CHCl$_3$)

IR (KBr) 3520, 1745, 1680, 1505, 1410 1325, 1155, 1035 cm$^{-1}$

NMR (CDCl$_3$) δ 0.82(3H, s, 18-H$_3$) 0.87(3H, d, J=6.8 Hz, 28-H$_3$) 0.93(3H, s, 19-H$_3$) 0.95(3H, d, J=6-7Hz, 21-H$_3$) 1.15 & 1.17(6H, each s, 26-H$_3$ & 27-H$_3$) 3.15(1H, dd, J$_1$=7.1 Hz, J$_2$=16.4 Hz, 9-H) 3.88(1H, m, 1-H) 4.90(1H, m, 3-H) 6.27 & 6.42(2H, AB$_q$, J=8.6 Hz, 6-H & 7-H) 7.30–7.42(5H, m, —Ar—H)

mass spectrum: m/e 430(M$^+$- triazoline, 8), 251(15), 177(44) 119(100)

EXAMPLE 12

(24S)-5,7-Ergostadiene-1α,3β,25-triol (IIa)

To a suspension of lithium aluminum hydride (0.40 g) in dry tetrahydrofuran (30 ml) was added a solution of (24S)-5α,8α-(4-phenyl-1,2-urazolo)-6-ergostene-1α,3β,25-triol (XIa) (0.44 g, 0.73 mmol) prepared in Example 10 in dry tetrahydrofuran (12 ml) and the mixture was stirred under reflux for 1.5 hrs. To the mixture was added under ice-cooling water (0.4 ml), 10% aqueous sodium hydroxide solution (0.4 ml) and water (1.2 ml) and the mixture was further stirred at room temperature for 30 minutes. Anhydrous magnesium sulfate was added and the mixture was stirred for 30 minutes. After filtration through celite, the filtrate was concentrated. The residue was recrystallized from tetrahydrofuran-ethanol to afford 0.22 g of the title compound (IIa).

m.p. 228°–231° C.

$[\alpha]_D^{22}$ −89° (c=0.11, THF)

IR (KBr) 3520, 3360, 3330, 1655, 1605, 1465, 1380, 1135, 1070, 1045 cm$^{-1}$

NMR (DMSO-D$_6$+CDCl$_3$) 0.60(3H, s, 18-H$_3$) 0.84(3H, d, J=6.6 Hz, 28-H$_3$) 0.85(3H, s, 19-H$_3$) 0.95(3H, d, J=6.1 Hz, 21-H$_3$) 1.07 & 1.08(6H, each s, 26-H$_3$ & 27-H$_3$) 3.62(1H, m, 1-H) 3.91(1H, m, 3-H) 5.30(1H, m, 7-H) 5.56 (1H, m, 6-H)

mass spectrum: m/e 430(M$^+$, 55) 412(85) 394(31) 251 (40) 197(64) 157(100) 145(68)

UV (EtOH) λ$_{max}$282 nm

EXAMPLE 13

(24R)-5,7-Ergostadiene-1α,3β,25-triol (IIb)

In a similar manner as in Example 12, 0.28 g of the title compound (IIb) was obtained from (24R)-5α,8α-(4-phenyl-1,2-urazolo)-6-ergostene-1α,3β,25-triol (XIb) (0.45 g, 0.74 mmol) prepared in Example 11.

m.p. 154°–157° C. (the crystals containing ½ EtOH)

$[\alpha]_D^{22}$ −17.4° (c=0.12, MeOH)

IR (KBr) 3400, 1655, 1605, 1465, 1385, 1155, 1055 cm$^{-1}$

NMR (CDCl$_3$) δ 0.63(3H, s, 18-H$_3$) 0.88(3H, d, J=6.6 Hz, 28-H$_3$) 0.95(3H, d, J=6.1 Hz) 0.95(3H, s, 19-H$_3$) 1.16 & 1.17(6H, each s, 26-H$_3$ & 27-H$_3$) 3.78(1H, m, 1-H) 4.08(1H, m, 3-H) 5.40(1H, m, 7-H) 5.73(1H, m, 6-H)

mass spectrum: m/e 430(M$^+$, 32) 412(20) 394(18) 251 (35) 197(64) 157(100) 145(65)

EXAMPLE 14

(24S)-1α,25-Dihydroxyvitamin D$_4$ (Ia)

(24S)-5,7-Ergostadiene-1α,3β,25-triol (IIa) (100 mg, 0.23 mmol) prepared in Example 12 was dissolved in a mixed solvent of ether (950 ml) and tetrahydrofuran (50 ml), and the solution was irradiated for 3 minutes with high pressure mercury lamp using 1.5% aqueous potassium nitrate solution as a filter under water-cooling in an argon gas stream. From the reaction solution was distilled off the solvent and the resultant residue containing previtamin D (XIIa) was dissolved in ethanol (25 ml) and the solution was stirred under reflux for one hour. After distilling off ethanol, the residue was purified by preparative high performance liquid chromatography (HPLC) [column: LiChrosorb® Si60 (7 μm), φ25×250 mm, Merck Co., Ltd.; column effluent: 6% methanol-methylene chloride; flow rate: 6.0 ml/min; detected at 265 nm] to give 25 mg of the title compound (Ia) which was recrystallized from hexane-methylene chloride.

m.p. 93°–95° C.

$[\alpha]_D^{22} +33°$ (c=0.15, EtOH)

NMR (CDCl₃) δ 0.54(3H, s, 18-H₃) 0.90(3H, d, J=6.8 Hz, 28-H₃) 0.94(3H, d, J=5.9 Hz, 21-H₃) 1.15 & 1.17(6H, each s, 26-H₃ & 27-H₃) 4.23(1H, m, 3-H) 4.43(1H, m, 1-H) 5.00 (1H, narrow m, 19-H) 5.33(1H, narrow m, 19-H) 6.02(1H, d, J=11.2 Hz, 7-H) 6.38 (1H, d, J=11.2 Hz, 6-H)

mass spectrum: m/e 430(M⁺, 8) 412(10) 394(11) 285 (6) 251(5) 134(100) 105(34)

UV (EtOH) λ_max 265 nm

EXAMPLE 15

(24R)-1α,25-Dihydroxyvitamin D₄ (Ib)

(24R)-5,7-Ergostadiene-1α,3β,25-triol (IIb) (100 mg, 0.23 mmol) prepared in Example 13 was dissolved in ether (1000 ml) and the solution was irradiated for 3 minutes with high pressure mercury lamp using 1.5% aqueous potassium nitrate solution as a filter under water-cooling in an argon gas stream. From the reaction solution was distilled off ether and the resultant residue was purified by preparative high performance liquid chromatography (HPLC) [column: LiChrosorb® Si60 (7 μm), φ25×250 mm, Merck Co., Ltd.; column effluent: 6% methanol-methylene chloride; flow rate: 6.0 ml/ml, detected at 265 nm] to give 25.0 mg of previtamin D (XIIb).

NMR (CDCl₃) δ 0.70(3H, s, 18-H₃) 0.88(3H, d, J=6.8 Hz, 28-H₃) 0.95(3H, d, J=6.1 Hz, 21-H₃) 1.17(6H, brs, 26-H₃ & 27-H₃) 1.77(3H, s, 19-H₃) 4.06(1H, m, 3-H) 4.20(1H, m, 1-H) 5.50(1H, m, 9-H) 5.78 & 5.92(2H, AB_q, J=12.2 Hz, 6-H & 7-H)

The previtamin D (XIIb) as prepared above was dissolved in ethanol (15 ml) and stirred under reflux for one hour. The residue obtained by distilling off ethanol was purified by preparative high performance liquid chromatography [column: LiChrosorb® Si60 (7 μm), φ25×250 mm, Merck Co., Ltd.; column effluent: 6% methanol-methylene chloride; flow rate: 6.0 ml/min, detected at 265 nm] to give 16.7 mg of the title compound (Ib) which was recrystallized from hexane-methylene chloride.

m.p. 172°–174° C.

$[\alpha]_D^{22} +63°$ (c=0.11, EtOH)

NMR (CDCl₃) δ 0.54(3H, s, 18-H₃) 0.88(3H, d, J=6.8 Hz, 28-H₃) 0.93(3H, d, J=6.1 Hz, 21-H₃) 1.16 & 1.17(6H, each s, 26-H₃ & 27-H₃) 4.23(1H, m, 3-H) 4.44(1H, m, 1-H) 5.01 (1H, narrow m, 19-H) 5.33(1H, narrow m, 19-H) 6.02(1H, d, J=11.2 Hz, 7-H) 6.38 (1H, d, J=11.2 Hz, 6-H)

mass spectrum: m/e 430(M⁺, 5) 412(11) 394(18) 285 (5) 251(5) 134(100) 105(32)

UV (EtOH) λ_max 265 nm

EXAMPLE 16

22-Iodo-5α,8α-(4-phenyl-1,2-urazolo)-23,24-dinor-6-cholene-1α,3β-diol diacetate (XX, hal=I)

A solution of 5α,8α-(4-phenyl-1,2-urazolo)-23,24-dinor-6-cholene-1α,3β,22-triol 1α,3β-diacetate 22-p-toluenesulfonate (V) (2.61 g, 3.44 mmol) obtained in a similar manner as in Example 2 and sodium iodide (2.57 g, 17.1 mmol) in dry N,N-dimethylformamide (20 ml) was stirred at 80° C. for 30 minutes. After cooling, the reaction solution was poured into water and extracted with chloroform. The chloroform layer was washed with water, 5% aqueous sodium thiosulfate solution and a saturated sodium chloride solution, dried over anhydrous magnesium sulfate and then concentrated. The residue was purified by silica gel chromatography (eluted with 3/2 and then 1/1 hexane/ethyl acetate) to give 2.33 g of the title compound (XX). A sample for analysis was prepared by recrystallization from hexane-ethyl acetate.

m.p. 173°–174° C.

$[\alpha]_D^{23} -64.4°$ (c=1.12, CHCl₃)

IR (KBr) 1740, 1685, 1600, 1505, 1410, 1250, 1230, 1030 cm⁻¹

NMR (CDCl₃) δ 0.87(3H, s, 18-H₃) 1.04(3H, d, J=6.6 Hz, 21-H₃) 1.06(3H, s, 19-H₃)

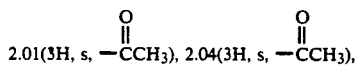

2.01(3H, s, —CCH₃), 2.04(3H, s, —CCH₃), 3.12–3.36(3H, m, 9-H & 22-H₂) 5.11(1H, m, 1-H) 5.88(1H, m, 3-H) 6.34 & 6.44(2H, AB_q, J=8.3 Hz, 6-H & 7-H) 7.28–7.51(5H, m, —Ar—H)

mass spectrum: m/e 540(M⁺- triazoline, 0.3), 480(8), 420(95), 251(20), 141(100), 119(65)

EXAMPLE 17

22-Iodo-5α,8α-(4-phenyl-1,2-urazolo)-23,24-dinor-6-cholene-1α,3β-diol (XXI, hal=I)

To 22-iodo-5α,8α-(4-phenyl-1,2-urazolo)-23,24-dinor-6-cholene-1α,3β-diol diacetate (XX) (1.23 g, 1.72 mmol) prepared in a similar manner as in Example 16 was added a solution of sodium hydroxide (0.14 g, 3.5 mmol) in methanol (20 ml) and the solution was stirred under reflux for 30 minutes. From the reaction solution was distilled off methanol under reduced pressure and the resultant residue to which was added water was extracted with chloroform. The chloroform layer was washed with a saturated sodium chloride solution, dried over anhydrous magnesium sulfate and then concentrated to give 1.05 g of the crude title compound (XXI) as the residue. A sample for analysis was prepared by recrystallization from chloroform-ethyl acetate.

m.p. 172°–174° C.

$[\alpha]_D^{23} -65.4°$ (c=1.14, CHCl₃)

IR (KBr) 3420, 1745, 1680, 1600, 1505, 1400, 1150, 1090, 1030 cm⁻¹

NMR (CDCl₃) δ 0.84(6H, brs, 18-H₃ & 19-H₃) 1.05(3H, d, J=5.6 Hz, 21-H₃) 3.02–3.35(3H, m, 9-H & 22-H₂) 3.70(1H, m, 1-H) 4.80 (1H, m, 3-H) 6.20 & 6.34(2H, AB_q, J=8.3 Hz, 6-H & 7-H) 7.29–7.40(5H, m, —Ar—H)

mass spectrum: m/e 456(M⁺- triazoline, 13), 438(5), 436(11), 420(10), 410(20), 328(5), 251(15), 177(68), 119(100)

EXAMPLE 18

22-Iodo-5α,8α-(4-phenyl-1,2-urazolo)-1α,3β-bis(tetrahydropyranyloxy)-23,24-dinor-6-cholene (XXII, hal=I)

A solution of the crude 22-iodo-5α,8α-(4-phenyl-1,2-urazolo)-23,24-dinor-6-cholene-1α,3β-diol (1.05 g) obtained in a similar manner as in Example 17, dihydropyran (0.43 g, 5.12 mmol), a catalytic amount of p-toluenesulfonic acid monohydrate in dry methylene chloride solution (20 ml) was stirred at room temperature for 24 hrs. The reaction solution was washed with a saturated sodium hydrogencarbonate solution and a saturated sodium chloride solution, dried over anhydrous magnesium sulfate and then concentrated. The residue was purified by silica gel chromatography (eluted with 2/1 hexane/ethyl acetate) to give 1.00 g of the title compound (XXII).

IR (KBr) 1750, 1690, 1600, 1505, 1400, 1130, 1115, 1030 cm$^{-1}$

NMR (CDCl$_3$) δ 0.87(3H, s, 18-H$_3$) 0.96 & 0.99(3H, pair of s, 19-H$_3$) 1.05(3H, d, J=5.9 Hz, 21-H$_3$)

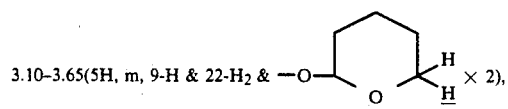
3.10-3.65(5H, m, 9-H & 22-H$_2$ & —O— ... ×2),

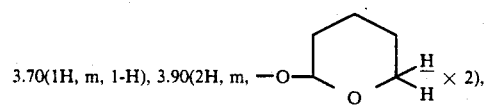
3.70(1H, m, 1-H), 3.90(2H, m, —O— ... ×2),

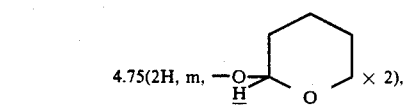
4.75(2H, m, —O— ... ×2), 4.95(1H, m, 3-H) 6.30 6.45(2H, m, 6-H & 7-H) 7.30–7.50(5H, m, —Ar—H)

mass spectrum m/e 624(M$^+$- triazoline, 0.8), 540(2), 454(10), 437(48), 420(23), 382(15), 309(10), 251(12), 177(48), 119(100)

EXAMPLE 19

(24R)-23ξ-Phenylsulfonyl-5α,8α-(4-phenyl-1,2-urazolo)-1α,3β,25-tris(tetrahydropyranyloxy)-6-ergostene (XXIIIa)

To a solution of (3R)-2,3-dimethyl-4-phenylsulfonyl-2-butanol tetrahydropyranyl ether (XXIVa) (326 mg, 1.0 mmol) in dry tetrahydrofuran (3 ml) was added successively n-butyllithium (1.5N hexane solution, 0.67 ml, 1.0 mmol) and dry hexamethylphosphoric triamide (0.17 ml, 1.0 mmol) at −78° C. under an argon gas stream and then the solution was stirred at −20° C. for 20 minutes. Subsequently, a solution of 22-iodo-5α,8α-(4-phenyl-1,2-urazolo)-1α,3β-bis(tetrahydropyranyloxy)-23,24-dinor-6-cholene (XXII) (400 mg, 0.50 mmol) obtained in a similar manner as in Example 18 in dry tetrahydrofuran (4 ml) was added at the same temperature and the mixture was stirred for 2 hrs and further stirred at room temperature for 2 hrs. The reaction solution was poured into a saturated ammonium chloride solution and extracted with chloroform. The chloroform layer was washed with a saturated sodium chloride solution, dried over anhydrous magnesium sulfate and then concentrated. The residue was purified by silica gel chromatography (eluted with 4/1 hexane/ethyl acetate) to give 317 mg of the title compound (XXIIIa).

IR (KBr) 1750, 1695, 1600, 1500, 1400, 1140, 1125, 1030 cm$^{-1}$

NMR (CDCl$_3$) δ

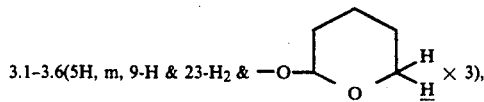
3.1-3.6(5H, m, 9-H & 23-H$_2$ & —O— ... ×3),

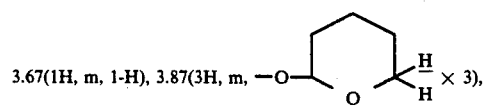
3.67(1H, m, 1-H), 3.87(3H, m, —O— ... ×3),

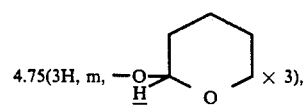
4.75(3H, m, —O— ... ×3), 4.95(1H, m, 3-H) 6.33(2H, m, 6-H & 7-H) 7.3–7.9(10H, m, —Ar—H)

mass spectrum: m/e 570(M$^+$-triazoline-dihydropyran×3.3) 552(4), 534(4), 177(57), 119(100)

EXAMPLE 20

(24S)-5α,8α-(4-Phenyl-1,2-urazolo)-1α,3β,25-tris(tetrahydropyranyloxy)-6-ergostene (Xa)

(24R)-23ξ-Phenylsulfonyl-5α,8α-(4-phenyl-1,2-urazolo)-1α,3β,25-tris(tetrahydropyranyloxy)-6-ergostene (XXIIIa) (300 mg, 0.30 mmol) prepared in Example 19 was dissolved in methanol (30 ml) saturated with disodium hydrogenphosphate, to which was added sodium amalgam (5%, 4.15 g, 9.0 mmol) and the mixture was stirred at room temperature for 17 hrs. Subsequently, the reaction solution was worked up in a similar manner as in Example 8 to give 90 mg of the title compound (Xa).

IR and NMR spectra of the compound (Xa) were consistent with those of the compound (Xa) prepared in Example 8.

REFERENTIAL EXAMPLE 1

(22E)-5α,8α-(4-Phenyl-1,2-urazolo)-6,22-ergostadiene-1α,3β-diol diacetate (XV)

To a solution of (22E)-5,7,22-ergostatriene-1α,3β-diol diacetate (XIV) (2.46 g, 5.0 mmol) in chloroform (20 ml) was added dropwise a solution of 4-phenyl-1,2,4-triazoline-3,5-dione (1.04 g, 6.0 mmol) in acetone (15 ml) with stirring at room temperature. The solvent was distilled off under reduced pressure from the reaction solution and the residue was purified by silica gel chromatography (eluted with 2/1 hexane/ethyl acetate) to give 3.0 g of the foamy title compound (XV).

[α]$_D^{25}$ −139° (c=1.09, CHCl$_3$)

IR (KBr) 1750, 1700, 1600, 1505, 1395, 1240, 1030 cm$^{-1}$

NMR (CDCl$_3$) δ 0.79 & 0.82 (6H, each d, J=3.7 Hz, 26-H$_3$ & 27-H$_3$) 0.84(3H, s, 18-H$_3$) 0.89(3H, d, J=6.8 Hz, 28-H$_3$) 1.02(3H, d, J=6.6 Hz, 21-H$_3$) 1.06(3H, s, 19-H$_3$)

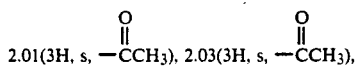

3.25 (1H, dd, $J_1=5.6$ Hz, $J_2=13.7$ Hz, 9-H) 5.11 (1H, m, 1-H) 5.20(2H, m, 22-H & 23-H) 5.89(1H, m, 3-H) 6.33 & 6.45(2H, AB$_q$, J=8.3 Hz, 6-H & 7-H) 7.24–7.51 (5H, m, —Ar—H̲)

mass spectrum m/e 671(M+, 0.3) 496(0.4) 436(8) 376 (100) 251(28) 209(23) 155(34)

REFERENTIAL EXAMPLE 2

22-Oxo-5α,8α-(4-phenyl-1,2-urazolo)-23,24-dinor-6-cholene-1α,3β-diol diacetate (III)

(22E)-5α,8α-(4-Phenyl-1,2-urazolo)-6,22-ergostadiene-1α,3β-diol diacetate (XV) (10.00 g, 14.9 mmol) obtained in a similar manner as in Referential Example 1 was dissolved in a mixed solution of 1% pyridine and methylene chloride (400 ml) and then ozone (0.07 mmol/min) was bubbled into the solution with stirring at −65° C. for 4.5 hrs. After ozone was expelled by passing an argon gas through the reaction solution, dimethyl sulfide (20 ml) was added dropwise at −65° C. over a period of 15 minutes. The solution was stirred at the same temperature for one hour, and gradually returned to room temperature over a period of one hour. The reaction solution was washed with 2% hydrochloric acid (400 ml), then a saturated sodium chloride solution and dried over anhydrous magnesium sulfate and then concentrated. The residue was purified by silica gel chromatography (eluted with 1/1 hexane/ethyl acetate) and then recrystallized from benzene to give 4.40 g of the title compound (III).

m.p. 191°–193° C.

$[\alpha]_D^{25} -131°$ (c=1.06, CHCl$_3$)

IR (KBr) 2720, 1740, 1685, 1605, 1505, 1405, 1370, 1250, 1230, 1035 cm$^{-1}$

NMR (CDCl$_3$) δ 0.87(3H, s, 18-H$_3$) 1.07(3H, s, 19-H$_3$) 1.14(3H, d, J=6.8 Hz, 21-H$_3$)

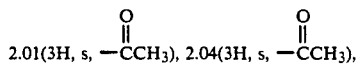

3.26(1H, dd, $J_1=5.4$ Hz, $J_2=14.2$ Hz, 9-H) 5.12(1H, m, 1-H) 5.88(1H, m, 3-H) 6.36 & 6.44(2H, AB$_q$, J=8.3 Hz, 6-H & 7-H) 7.26–7.51(5H, m, —Ar—H̲) 9.55(1H, d, J=3.4 Hz, 22-H)

mass spectrum: m/e 603(M+, 0.3) 428(0.3) 368(11) 308 (100) 235(20) 177(20) 141(57)

REFERENTIAL EXAMPLE 3

(S)-2,3-Dimethyl-1,3-butanediol (XVIIa)

A solution of methyl (S)-(+)-3-hydroxy-2-methylpropionate (8.09 g, 68.6 mmol), dihydropyran (8.63 g, 0.10 mol), p-toluenesulfonic acid monohydrate (0.10 g) in dry ether (50 ml) was stirred at room temperature for one hour. The reaction solution was poured into a saturated sodium hydrogencarbonate solution. The ether layer was washed with a saturated sodium chloride solution, dried over anhydrous magnesium sulfate and then concentrated to give 13.8 g of the crude tetrahydropyranyl ether as the residue.

From magnesium powder (5.00 g, 0.21 mol) in dry ether (20 ml) and a solution of methyl iodide (29.2 g, 0.21 mol) in dry ether (30 ml) was prepared Grignard reagent. To this Grignard reagent solution was added dropwise a solution of tetrahydropyranyl ether (13.8 g) in dry ether (30 ml) with stirring under mild reflux over a period of one hour. Thereafter, the solution was further stirred under reflux for 2 hrs. A cooled saturated ammonium chloride solution was added carefully by portions to the reaction solution under ice-cooling. The ether layer was separated and the aqueous layer was further extracted with ether. The combined ether layer was washed with a saturated sodium chloride solution, dried over anhydrous magnesium sulfate and then concentrated to give 13.5 g of the crude alcohol product as the residue.

IR (film) 3460, 1460, 1390, 1205, 1180, 1125, 1080, 1060, 1030, 980 cm$^{-1}$

A solution of the crude alcohol product (13.5 g) and p-toluenesulfonic acid monohydrate (0.65 g, 3.4 mmol) in methanol (150 ml) was stirred at room temperature for one hour. After neutralized with potassium carbonate, the solution was filtered through Celite and methanol was distilled off under reduced pressure. The residue was dissolved in ether, dried over anhydrous magnesium sulfate and then concentrated. The residue was purified by distillation to give 6.28 g of the title compound (XVIIa).

b.p. 83°–85° C./0.22 mmHg $n_D^{23}$ 1.4439

$[\alpha]_D^{23} +1.7°$ (c=5.12, CHCl$_3$)

IR (film) 3350, 1470, 1385, 1370, 1175, 1160, 1030 cm$^{-1}$

NMR (CDCl$_3$) δ 0.84(3H, d, J=7.1 Hz) 1.18(3H, s) 1.25 (3H, s) 1.81(1H, m) 3.70(1H, m) 3.91 (1H, s) 4.17(1H, t, J=4.6 Hz)

REFERENTIAL EXAMPLE 4

(3R)-4-Iodo-2,3-dimethyl-2-butanol tetrahydropyranyl ether (XIIIa)

To a solution of (S)-2,3-dimethyl-1,3-butanediol (XVIIa) (6.40 g, 54.2 mmol) obtained in a similar manner as in Referential Example 3 in dry pyridine (25 ml) was added p-toluenesulfonyl chloride (12.40 g, 65.1 mmol) under ice-cooling and the solution was stirred at the same temperature for one hour. To the reaction solution was added water at the same temperature and the solution was stirred for 30 minutes. The reaction solution was poured into ice-water and extracted with ether. The ether layer was washed successively with water, a saturated cupric sulfate solution, a saturated sodium hydrogencarbonate solution and a saturated sodium chloride solution, dried over anhydrous magnesium sulfate and then concentrated. A solution of the resultant residue containing the tosylate (XVIIIa) and sodium iodide (24.4 g, 0.16 mol) in acetone (180 ml) was stirred under reflux for 5 hrs. Acetone was distilled off from the reaction solution, water was added to the residue and the mixture was extracted with ether. The ether layer was washed with 10% sodium thiosulfate solution and a saturated sodium chloride solution, dried over anhydrous magnesium sulfate and then concentrated. The residue was purified by distillation to afford 8.62 g of (R)-4-iodo-2,3-dimethyl-2-butanol (XIXa).

b.p. 69°–71° C./4 mmHg $n_D^{25}$ 1.5192

$[\alpha]_D^{23} -37.7°$ (c=1.98, CHCl$_3$)

IR (film) 3400, 1470, 1380, 1190, 1135, 1110, 950 cm$^{-1}$

NMR (CDCl$_3$) δ 1.11(3H, d, J=6.8 Hz) 1.16(3H, s) 1.26 (3H, s) 1.69(1H, s) 1.87(1H, m) 2.91 (1H, dd, $J_1=10.5$ Hz, $J_2=9.5$ Hz) 3.67 (1H, dd, $J_1=7.2$ Hz, $J_2=9.5$ Hz)

A solution of the resultant compound (XIXa) (7.73 g, 33.9 mmol), dihydropyran (5.70 g, 67.8 mmol) and pyridinium p-toluenesulfonate (0.85 g, 3.4 mmol) in dry methylene chloride (70 ml) was stirred at room temperature for 3 hrs. The reaction solution was washed with a saturated sodium hydrogencarbonate solution and a saturated sodium chloride solution, dried over anhydrous magnesium sulfate and then concentrated. The residue was purified by silica gel chromatography (eluted with 19/1 hexane/ether) to give 9.88 g of the title compound (XIIIa).

IR (film) 1470, 1390, 1375, 1200, 1130, 1075, 1035, 1025, 985 cm$^{-1}$

REFERENTIAL EXAMPLE 5

(R)-2,3-Dimethyl-1,3-butanediol (XVIIb)

In a similar manner as in Referential Example 3, 7.61 g of the title compound (XVIIb) was prepared from methyl (R)-(−)-3-hydroxy-2-methylpropionate (9.28 g, 78.6 mmol).

b.p. 83°–84° C./0.25 mmHg
$n_D^{23}$ 1.4437
$[\alpha]_D^{23} -1.6°$ (c=5.29, CHCl$_3$)

IR and NMR spectra of this compound were consistent with those of the compound (XVIIb).

REFERENTIAL EXAMPLE 6

(3S)-4-Iodo-2,3-dimethyl-2-butanol tetrahydropyranyl ether (XIIIb)

In a similar manner as in Referential Example 4, 10.20 g of (S)-4-iodo-2,3-dimethyl-2-butanol (XIXb) was prepared from (R)-2,3-dimethyl-1,3-butanediol (XVIIb) (6.85 g, 58.1 mmol) obtained similarly to Referential Example 5.

b.p. 69°–71° C./4 mmHg
$n_D^{23}$ 1.5190
$[\alpha]_D^{23} +38.7°$ (c=1.93, CHCl$_3$)

IR and NMR spectra of this compound were consistent with those of the compound (XIXa).

In a similar manner as in Referential Example 4, 10.88 g of the title compound (XIIIb) was prepared from the compound (XIXb) (8.60 g, 37.7 mmol) as obtained above.

IR spectrum of this compound was consistent with that of the compound (XIIIa).

What is claimed is:

1. A 1α,25-dihydroxyvitamin D$_4$ compound of formula (I)

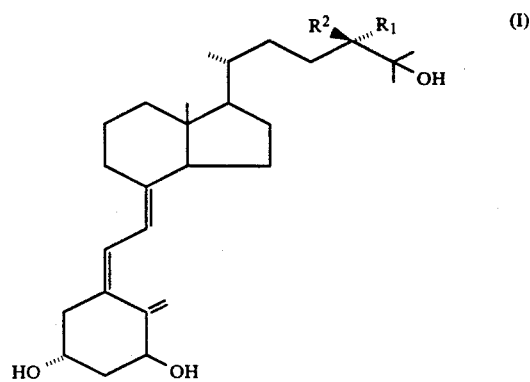

wherein R$_2$ is H when R$_1$ is CH$_3$ (24S form) or R$_2$ is CH$_3$ when R$_1$ is H (24R form).

* * * * *